United States Patent [19]

Yasuda et al.

[11] 4,346,098
[45] Aug. 24, 1982

[54] FUNGICIDAL COMPOSITIONS AND METHODS

[75] Inventors: Yasushi Yasuda, Yokohama; Masami Mizuno, Yamanishi; Hiroaki Nishikawa, Ohiso; Akira Murakami, Hiratsuka, all of Japan

[73] Assignee: Nippon Soda Company Limited, Tokyo, Japan

[21] Appl. No.: 213,452

[22] Filed: Dec. 5, 1980

[30] Foreign Application Priority Data

Dec. 7, 1979 [JP] Japan .................. 54/158108

[51] Int. Cl.³ ...................... A01N 43/50; A01N 43/56
[52] U.S. Cl. .............................................. 424/273 R
[58] Field of Search ..................... 424/273 R

[56] References Cited

U.S. PATENT DOCUMENTS 4,085,209  4/1978  Miller et al. .................. 424/273 R
4,208,411  6/1980  Katsuyata et al. ............. 424/273 R

FOREIGN PATENT DOCUMENTS 1806123  6/1969  Fed. Rep. of Germany .

*Primary Examiner*—Jerome D. Goldberg
*Assistant Examiner*—F. J. Moezie
*Attorney, Agent, or Firm*—George B. Oujevolk

[57] ABSTRACT

A fungicidal composition containing as the active component a mixture of (I) a compound having the formula of

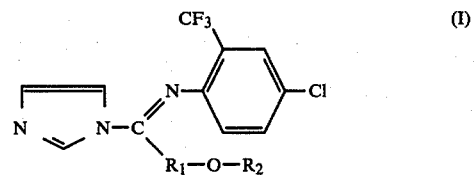

(I)

wherein
$R_1$ is methylene or $C_{2-4}$ alkylene, and
$R_2$ is $C_{1-4}$ alkyl, and
(II) a compound having the formula of

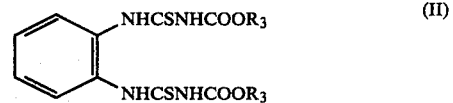

(II)

wherein $R_3$ is $C_{1-2}$ alkyl.

4 Claims, No Drawings

FUNGICIDAL COMPOSITIONS AND METHODS

This invention relates to new fungicidal compositions having enhanced effectiveness and to improved methods of controlling fungus growths.

Many of fungicidal compositions used for agricultural and horticultural purposes have the disadvantage of limited effectiveness against one or more spieces of fungus, and are frequently encountered by appearance of fungus resistant to fungicides. It is often not possible to apply greater amounts of fungicides to overcome these difficulties, since increased quantities of fungicides may endanger the growth of wanted plants, and residues from the use of excessive quantities of fungicides may result in injury to men and animals.

It is an object of this invention to provide fungicidal compositions for agricultural and horticultural usages of increased effectiveness. It is a further object to provide improved and more efficacious methods for controlling fungus growths.

The fungicidal composition of the invention contains as the fungicidal component a mixture of (I) a compound having the formula of

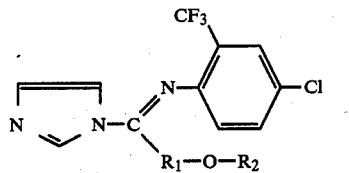

wherein
$R_1$ is methylene or $C_{2-4}$ alkylene, and
$R_2$ is $C_{1-4}$ alkyl,
and
(II) a compound having the formula of

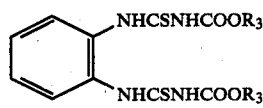

wherein $R_3$ is $C_{1-2}$ alkyl, in a weight ratio of compound (I) and compound (II) of 95:5 to 5:95.

The compound (I) is disclosed in, for example, the U.S. Pat. No. 4,208,411, as a fungicidally active compound, and the compound (II) is known as a systemic fungicide THIOPHANATES. Among the compounds, 1-[N-(4-chloro-2-trifluoromethylphenyl)-2-propoxyacetoimidoyl]imidazole in the compound (I) and dimethyl-4,4'-o-phenylene-bis-3-thioallophanate in the compound (II) are the most preferred compounds to constituents of the mixed fungicidal component.

Weight ratios of the constituents in the mixed fungicidal component may vary in accordance with application methods of the fungicidal composition, and the ratio of compound (I) to compound (II) ranges from 95:5 to 5:95. However, the ratio may be settled at around 70:30 to 10:90 for fungicidal compositions of ordinary application methods.

The mixed fungicidal component may be applied directly to plant without being formulated, however, the active component is preferably formulated by mixing it with suitable carriers and others into conventional forms of pesticidal compositions such as wettable powder, dust and flowable.

The concentration of the active component in the fungicidal composition varies according to types of formulation, and is, for example, 5 to 80 weight percent, preferably 10 to 50 weight percent for wettable powder formulations and 0.5 to 20 weight percent, preferably 1 to 10 weight percent for dust formulations.

The method for control of fungus growths contemplated herein comprises applying the fungicidal composition described herein in an amount sufficient to exert fungicidal action to a locus to be protected. Usually, the fungicidal composition is applied to plant foliage at a rate of around 100 g of the active component per 10 acres, preferably 150 g or over per 10 acres.

Because of the enhanced fungicidal activity of the compositions, it is possible by their use to control a wider variety of plant diseases in vegetables, fruit and other crops in smaller amount of application rate compared with the individual constituent of the active component. Furthermore, the compositions do not show phytotoxicity when applied to plants. Among plant diseases controlled effectively by spraying of the composition are grey mold, fruit rot, damping off and powdery mildew of vegetables; brown rot of peach; leaf spot of corn; scab and powdery mildew of pear and apple; and grey mold of grape. The composition has not only usages for foliar spray on plant diseases, but is also used for treatments of soil and plant seeds.

Some non-limiting examples of fungicidal compositions according to the invention are as follows:

| Example 1: Wettable Powder | |
|---|---|
| Compound (I) | 20 parts by weight |
| Compound (II) | 40 parts by weight |
| White carbon | 5 parts by weight |
| Diatomaceous earth | 25 parts by weight |
| Sodium polyoxyethylenealkylsulfate | 10 parts by weight |

These are mixed and pulverized to provide homogeneous fine powders. In use, the powder is diluted with water to a suspension of the desired concentration.

| Example 2: Wettable Powder | |
|---|---|
| Compound (I) | 30 parts by weight |
| Compound (II) | 15 parts by weight |
| Diatomaceous earth | 43 parts by weight |
| Sodium higheralcoholsulfate | 5 parts by weight |
| Alkylnaphthalene sulfonic acid | 3 parts by weight |

| Example 3: Dust Formulation | |
|---|---|
| Compound (I) | 3 parts by weight |
| Compound (II) | 5 parts by weight |
| Talc | 46 parts by weight |
| Clay | 46 parts by weight |

These are mixed and pulverized to provide homogeneous fine powders. The formulation is applied directry.

| Example 4: Flowable Formulation | |
|---|---|
| Compound (I) | 3 parts by weight |
| Compound (II) | 30 parts by weight |
| Sodium polyoxyethylenealkylsulfate | 8 parts by weight |
| Glycerin | 5 parts by weight |

-continued

| | |
|---|---|
| Water | 54 parts by weight |

The formulation is applied directly or after dilution with water.

The fungicidal activity of compositions of this invention is illustrated by the following tests. In the tests, compound (A) denotes 1-[N-(4-chloro-2-trifluoromethylphenyl)-2-propoxyacetoimdoyl] imidazole, and compound (B) denotes dimethyl -4,4'-o-phenylene-bis-thioallophanate.

Test 1: Test for control of Gray Mold of Bean

Aqueous suspensions having desired concentrations of compound (A) and compound (B) respectively were prepared by diluting with water wettable powder formulations containing varied amount of each compound.

Leaves of kidney bean seedling (variety: Nagauzura) grown in a pot for about 3 weeks were sprayed with the aqueous suspension (25 ml/2 seedlings).

After a week, the treated leaves were detached and inoculated with mycelia of *Botrytis cinerea*. The inoculated leaves were kept for 4 days at 20° C., and the degree of disease was checked. The effectiveness of the treatment was evaluated by comparing the diseased area in the treated leaves with that in untreated leaves.

Table 1 shows the result conducted against the mycelia susceptible to compound (B), and Table 2 shows the result against the mycelia resistant to compound (B).

In relation to Table 1, percent of control of a comparative fungicidal composition EUPAREN at 200 ppm active ingredient was 58%.

TABLE 1

| | | Concentration of compound (B) (ppm) | | | |
|---|---|---|---|---|---|
| | | 50 | 25 | 12.5 | 0 |
| Concentration of compound (A) (ppm) | 50 | 100% | 100 | 100 | 53 |
| | 25 | 100 | 99 | 100 | 24 |
| | 12.5 | 98 | 100 | 96 | 12 |
| | 0 | 62 | 41 | 36 | 0* |

*Control over untreated leaves

TABLE 2

| | | Concentration of compound (B) (ppm) | | | | | |
|---|---|---|---|---|---|---|---|
| | | 100 | 100 | 50 | 25 | 12.5 | 0 |
| Concentration of compound (A) (ppm) | 50 | 100% | 100 | 100 | 100 | 100 | 80 |
| | 25 | 100 | 100 | 100 | 100 | 97 | 65 |
| | 12.5 | 97 | 100 | 95 | 92 | 88 | 54 |
| | 0 | 8 | 14 | 3 | 0 | 0 | 0 |

Test 2: Test for control of Apple Scab

Leaves of potted apple seedlings (variety: Kokko) were sprayed with an aqueous suspension containing desired amount of each compound at a rate of 10 ml per pot planted with 3 seedlings.

After the leaves were air-dried, they were inoculated with conidia of *Venturia inaequalis*, and held in a humid room of 20° C. for 2 days. Then, the seedlings were kept in a greenhouse of 20° C., and on the 14th day after the inoculation, effectiveness of the treatment was evaluated. The results are shown in Table 3. In relation to Table 3, percent of control of a comparative fungicidal composition CYPREX at 100 ppm active ingredient was 73%.

TABLE 3

| | | Concentration of compound (B) (ppm) | | | | |
|---|---|---|---|---|---|---|
| | | 50 | 25 | 12.5 | 6.2 | 0 |
| Concentration of compound (A) (ppm) | 12.5 | 100% | 100 | 100 | 96 | 52 |
| | 6.2 | 100 | 99 | 100 | 88 | 43 |
| | 3.1 | 85 | 90 | 79 | 62 | 19 |
| | 0 | 75 | 51 | 25 | 20 | 0 |

Test 3: Test for control of Cucumber Powdery Mildew

Leaves of a potted cucumber seedling (Variety: Satsukimidori) was sprayed with an aqueous suspension containing desired amount of each compound (5 ml/seedling).

After the treated seedlings were held in a greenhouse for a week, the leaves were inoculated with conidia of *Sphaerotheca fuliginea* resistant to compound (B), and the seedlings were kept for 9 days in a greenhouse at 25° C. The results are shown in Table 4.

TABLE 4

| Concentration of active component | | Control effect |
|---|---|---|
| Compound (A) | Compound (B) | (%) |
| 12.5 ppm | 0 | 57 |
| 6.2 | 0 | 31 |
| 3.1 | 0 | 20 |
| 0 | 100 | 31 |
| 0 | 50 | 18 |
| 0 | 25 | 0 |
| 12.5 | 100 | 100 |
| 6.2 | 50 | 98 |
| 6.2 | 25 | 98 |
| 3.1 | 50 | 79 |
| 3.1 | 25 | 67 |
| MORESTAN (100 ppm) | | 50 |

Test 4: Test for control of "Bakanae" disease of rice by seed treatment

Rice seeds (variety:: Kinki No. 33) infested by *Gibberella fujikuroi* were soaked in water for 4 days, and then dipped for 10 minutes in an aqueous suspension containing desired amount of each compound.

Then, the rice seeds were incubated for 20 hours at 30° C. by wrapping in a wet towel to obtain uniformly germinating seeds. In a plant-bed of 200 cm² area, 100 germinated seeds were sowed, and the control effect was evaluated 42 days after sowing. The result obtained in duplicate tests is shown in Table 5.

TABLE 5

| Concentration of active component | | Diseased seedling | Control effect* |
|---|---|---|---|
| Compound (A) | Compound (B) | (%) | (%) |
| 1,000 ppm | 0 | 49.2 | 21 |
| 500 | 0 | 50.3 | 19 |
| 0 | 5,000 | 21.8 | 65 |
| 0 | 2,500 | 27.9 | 55 |
| 1,000 | 5,000 | 1.9 | 97 |
| 1,000 | 2,500 | 6.7 | 90 |
| 500 | 5,000 | 7.1 | 89 |
| 500 | 2,500 | 9.1 | 85 |
| Untreated | | 61.9 | 0 |

*100 × (1 − % of diseased seedling grown from treated seeds / % of diseased seedling grown from untreated seeds)

We claim:

1. A fungicidal composition for agricultural and horticultural use consisting essentially of an inert carrier and a fungicidally effective amount of a mixture of compounds (I) and (II) in a weight ratio of compound (I) and compound (II) of 80:20 to 5:95, said compounds having the following structural formulas:

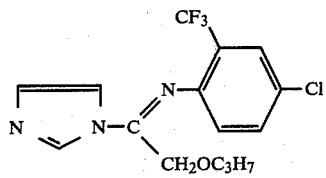

(I)

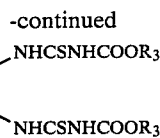

(II)

wherein $R_3$ is an alkyl component having 1 or 2 carbon atoms.

2. A fungicidal composition as claimed in claim 1 wherein compound II is dimethyl-4,4'-o-phenylene-bis-3-thioallophanate.

3. A method of controlling fungus comprising applying a fungicidal composition of claim 1 in an amount sufficient to exert fungicidal action to a locus to be protected.

4. A method of controlling fungus comprising applying a fungicidal composition of claim 2 in an amount sufficient to exert fungicidal action to a locus to be protected.

* * * * *